US009968284B2

(12) United States Patent
Vidalis et al.

(10) Patent No.: US 9,968,284 B2
(45) Date of Patent: May 15, 2018

(54) ANTI-INTERFERENT BARRIER LAYERS FOR NON-INVASIVE TRANSDERMAL SAMPLING AND ANALYSIS DEVICE

(71) Applicant: Flexible Medical Systems, LLC, Rockville, MD (US)

(72) Inventors: Joseph J Vidalis, Bethesda, MD (US); Joseph A Marcanio, Greensburg, PA (US); John Frederick Currie, Bethesda, MD (US); Sundar Nadarajan, Ashburn, VA (US); Helena Woodvine, Takoma Park, MD (US)

(73) Assignee: CLINITECH, LLC, Carson City, NV (US)

( * ) Notice: Subject to any disclaimer, the term of this patent is extended or adjusted under 35 U.S.C. 154(b) by 1448 days.

(21) Appl. No.: 13/688,954

(22) Filed: Nov. 29, 2012

(65) Prior Publication Data

US 2013/0144142 A1 Jun. 6, 2013

Related U.S. Application Data

(60) Provisional application No. 61/566,511, filed on Dec. 2, 2011.

(51) Int. Cl.
*A61B 5/05* (2006.01)
*A61B 5/145* (2006.01)
(Continued)

(52) U.S. Cl.
CPC ........ *A61B 5/14514* (2013.01); *A61B 5/1477* (2013.01); *A61B 5/1486* (2013.01);
(Continued)

(58) Field of Classification Search
CPC ............ A61B 5/14514; A61B 5/15134; A61B 5/150022; A61B 5/1486; A61B 5/1491;
(Continued)

(56) References Cited

U.S. PATENT DOCUMENTS 4,526,176 A 7/1985 Bremer et al.
4,775,361 A 10/1988 Jacques et al.
(Continued)

FOREIGN PATENT DOCUMENTS

EP 1 003 033 A1 5/2000
WO 97/19344 A1 5/1997
(Continued)

OTHER PUBLICATIONS

International Preliminary Report on Patentability for International Application No. PCT/US2012/067265, dated Jun. 12, 2014.
(Continued)

*Primary Examiner* — Tiffany Weston
*Assistant Examiner* — Tho Tran
(74) *Attorney, Agent, or Firm* — The Marbury Law Group, PLLC (57) ABSTRACT

A system and methods are provided for reducing electrochemical interference in a transdermal sampling and analysis device. A one-step transdermal glucose biosensor may calculate glucose concentrations that are artificially high compared to traditional home blood glucose sensors due to interference, which may be mitigated by forming an anti-interferent barrier layer over a sensing element. The anti-interferent barrier layer may be formed over a sensing layer and may possess a charge type which repels interferent molecules having the same charge type from interacting with the sensing layer disposed below the anti-interferent barrier layer.

19 Claims, 7 Drawing Sheets

(51) Int. Cl.
*A61B 5/1477* (2006.01)
*A61B 5/1486* (2006.01)
*A61B 5/1491* (2006.01)
*A61B 5/151* (2006.01)
*A61B 5/15* (2006.01)
*A61B 5/155* (2006.01)
*A61B 5/157* (2006.01)

(52) U.S. Cl.
CPC ........ *A61B 5/1491* (2013.01); *A61B 5/14532* (2013.01); *A61B 5/150022* (2013.01); *A61B 5/15134* (2013.01); *A61B 5/155* (2013.01); *A61B 5/157* (2013.01); *A61B 5/150969* (2013.01)

(58) Field of Classification Search
CPC .............. A61B 5/1477; A61B 5/14532; A61B 5/150969; A61B 5/155; A61B 5/157
See application file for complete search history.

(56) References Cited

U.S. PATENT DOCUMENTS

| | | | |
|---|---|---|---|
| 4,821,733 A | 4/1989 | Peck | |
| 4,909,256 A | 3/1990 | Peck | |
| 5,019,034 A | 5/1991 | Weaver et al. | |
| 5,123,902 A | 6/1992 | Muller et al. | |
| 5,149,629 A | 9/1992 | Rishpon et al. | |
| 5,176,881 A | 1/1993 | Sepaniak et al. | |
| 5,203,327 A | 4/1993 | Schoendorfer et al. | |
| 5,284,748 A | 2/1994 | Mroczkowski et al. | |
| 5,330,527 A | 2/1994 | Mroczkowski et al. | |
| 5,362,307 A | 7/1994 | Montecalvo et al. | |
| 5,366,454 A | 11/1994 | Currie et al. | |
| 5,380,272 A | 1/1995 | Gross | |
| 5,458,140 A | 10/1995 | Eppstein et al. | |
| 5,711,861 A | 1/1998 | Ward et al. | |
| 5,722,397 A | 3/1998 | Eppstein | |
| 5,730,714 A | 3/1998 | Guy et al. | |
| 5,885,211 A | 3/1999 | Eppstein et al. | |
| 5,983,131 A | 11/1999 | Weaver et al. | |
| 5,985,116 A * | 11/1999 | Ikeda | C12Q 1/001 204/290.11 |
| 6,022,316 A | 2/2000 | Eppstein et al. | |
| 6,046,051 A * | 4/2000 | Jina | G01N 33/4905 422/403 |
| 6,056,738 A | 5/2000 | Marchitto et al. | |
| 6,124,597 A | 9/2000 | Shehada et al. | |
| 6,144,869 A | 11/2000 | Berner et al. | |
| 6,233,471 B1 | 5/2001 | Berner et al. | |
| 6,270,651 B1 | 8/2001 | Essalik et al. | |
| 6,342,037 B1 | 1/2002 | Roe et al. | |
| 6,393,318 B1 | 5/2002 | Conn et al. | |
| 6,464,687 B1 | 10/2002 | Ishikawa et al. | |
| 6,597,946 B2 | 7/2003 | Avrahami et al. | |
| 6,730,200 B1 * | 5/2004 | Stewart | C12Q 1/002 204/403.06 |
| 6,922,578 B2 | 7/2005 | Eppstein et al. | |
| 6,922,586 B2 | 7/2005 | Davies | |
| 7,001,495 B2 | 2/2006 | Thomas | |
| 2001/0052459 A1 | 12/2001 | Essalik et al. | |
| 2002/0051975 A1* | 5/2002 | Li | G01N 33/5438 435/6.11 |
| 2003/0100040 A1* | 5/2003 | Bonnecaze | A61B 5/0031 435/14 |
| 2003/0130616 A1 | 7/2003 | Steil et al. | |
| 2003/0208152 A1 | 11/2003 | Avrahami et al. | |
| 2003/0225362 A1 | 12/2003 | Currie et al. | |
| 2004/0157319 A1 | 8/2004 | Keen | |
| 2004/0180391 A1* | 9/2004 | Gratzl | A61B 5/14528 435/14 |
| 2004/0193219 A1 | 9/2004 | Asano et al. | |
| 2004/0253304 A1 | 12/2004 | Gross et al. | |
| 2005/0045476 A1* | 3/2005 | Neel | C12Q 1/006 204/403.02 |
| 2005/0069454 A1 | 3/2005 | Bell | |
| 2005/0182307 A1 | 8/2005 | Currie et al. | |
| 2005/0226921 A1 | 10/2005 | Kortzebom | |
| 2010/0160755 A1* | 6/2010 | Oviatt | A61B 5/14532 600/345 |
| 2012/0181189 A1* | 7/2012 | Merchant | C12Q 1/001 205/777.5 |

FOREIGN PATENT DOCUMENTS

| | | |
|---|---|---|
| WO | 99/56613 A1 | 11/1999 |
| WO | 2006/050032 A2 | 5/2006 |
| WO | 97/42882 A1 | 11/2007 |
| WO | 2011/053715 A2 | 5/2011 |

OTHER PUBLICATIONS

International Search Report and Written Opinion issued in PCT Application No. PCT/US2012/067265, dated Mar. 28, 2013.
International Search Report and Written Opinion, PCT/US05/44287, 5 pages, dated Aug. 28, 2006.
Preliminary Examination Report, PCT/USO 1/17081, 5 pages, dated Sep. 17, 2004.
Balabanova et al., "Detection of Drugs in Sweat (Nachweis von Drogen im schweib)" Beitr. Gerichtl. Med., vol. 48, pp. 45-49, 1990.
Henderson et al., "Excretion of Methadone and Metabolites in Human Sweat," Research Communications in Chemical Pathology and pharmacology, vol. 5, No. 1, pp. 1-8, Jan. 1973.
Peck et al., "Outward Transcutaneous Chemical Migration: Impliations for Diagnostics and Dosimetry", Skin Pharmacol., vol. 1, No. I, pp. 14-23, 1988.
Phillips et al., "A Sweat-Patch Test for Alcohol Consumption: Evaluation in Continuous and Episodic Drinkers", Alcohol: clinical and Experimental research, vol. 4, No. 4, pp. 391-395,1980.
"SpectRx an Innovactive Medical Technology Company" [online], Copyright 2004 [retrieved on Aug. 31, 2004], 1 p., Retrieved from the Internet: hhtp://www.spectrx.com.
Schneider et al., "B-Fit System: Bio-Flips Integrable Transdermal MicroSystem", ARO Workshop on Biomolecular Signaling, Energy Transfer, and Transduction Processes, Cashiers, NC, 16 pages, May 14-17, 2000.
Smith et al., "Cocaine in Hair, Saliva, Skin Swabs, and Urine of Cocaine Users' Children", Forensic Science International, vol. 83, pp. 179-189,1996.
Currie et al., "Novel Non-Intrusive Trans-Dermal Remote Wireless Micro-Fluidic Monitoring System Applied to Continuous Glucose and Lactate Assays for Casualty Care and Combat Readiness," NATO: RTO-MP-HFM-109, pp. 24-1-24-17 (2004).
Nijdam, A.J., et al., "Fluidic encapsulation in SU-8 [micro]-reservoirs with [micro]-fluidic through-chip channels", Sensors and Actuators A, vol. 120, Apr. 29, 2005, p. 172-183.
Gadre et al., "Fabrication of a fluid encapsulated dermal patch using multilayered SU-8," Sensors and Actuators A: Physical, 114(2-3):478-485 (2004).
Paranjape et al., "A PDMS dermal patch for non-intrusive transdermal glucose sensing," Sensors and Actuators A: Physical, 104(3):195-204 (2003).
European Search Report dated Apr. 29, 2009, issued in US Application No. PCT/US2006023194, dated May 13, 2009.
Information Disclosure Statement filed on Oct. 20, 2008 in related U.S. Appl. No. 11/721,287.
Non-Final Office Action with List of References cited by the Examiner dated Dec. 3, 2010 issued in U.S. Appl. No. 11/721,287.
Non-Final Office Action with List of References cited by the Examiner dated Jan. 27, 2012 issued in U.S. Appl. No. 11/721,287.
Notice of Allowance and Fee(s) Due with Examiners Amendment, issued Aug. 16, 2012 in related U.S. Appl. No. 11/721,287.
Information Disclosure Statement filed Sep. 22, 2008 in related U.S. Appl. No. 12/096,769.
Information Disclosure Statement filed Aug. 12, 2009 in related U.S. Appl. No. 12/096,769.

(56) References Cited

OTHER PUBLICATIONS

Non-Final Office Action with List of References cited by the Examiner dated Aug. 11, 2011 in related U.S. Appl. No. 12/096,769.
Notice of Allowance and Fee(s) Due with Reasons for Allowance, issued Aug. 30, 2012 in related U.S. Appl. No. 12/096,769.
Information Disclosure Statement filed Jun. 18, 2012 in related U.S. Appl. No. 13/294,368.
Information Disclosure Statement filed Sep. 11, 2012 in related U.S. Appl. No. 13/609,838.
International Search Report with Written Opinion, PCT/US2011/06558, 15 pages, issued Jul. 25, 2012, dated Jul. 27, 2012.
S. Merchant et al., High-Sensitivity Amperometric Biosensors Based on Ferrocene-Modified Linear Poly (ethylenimine), Langmuir Article, 2009 American Chemical Society, Mar. 24, 2009.
Stephen A Merchant et al., (2010), Effect of Mediator Spacing on Electrochemical and Enzymatic Response of Ferrocene Redox Polymers, J. Phys. Chem., 114, 11627-11634.
Jian-Ping Xu et al (2008), Construction of phospholipid anti-biofouling multilayer on biomedical PET surfaces, Applied Surface Science 255, 538-540.
Maria G Carneiro-da Cunha et al (2010), Physical and thermal properties of a chitosan/alginate nanolayered PET film, Carbohydrate Polymers 82, 153-159.
Adam Heller et al., Electrochemical Glucose Sensors and Their Applications in Diabetes Management, Chem Review, Department of Chemical Engineering, Univ of Texas at Austin, Sep. 17, 2007.

\* cited by examiner

ANTI-INTERFERENT BARRIER LAYERS FOR NON-INVASIVE TRANSDERMAL SAMPLING AND ANALYSIS DEVICE

RELATED APPLICATIONS

This application claims priority to U.S. Provisional Patent Application No. 61/566,511 entitled "Anti-Interferent Barrier Layers for Non-Invasive Transdermal Glucose Measuring Devices" filed on Dec. 2, 2011, the entire contents of which are hereby incorporated by reference for all purposes. This application is related to U.S. patent application Ser. No. 13/609,838 entitled "Transdermal Sampling and Analysis Device," filed on Sep. 11, 2012, which is a continuation-in-part of U.S. patent application Ser. No. 13/294,368 entitled "Transdermal Sampling and Analysis Device/" filed on Nov. 11, 2011, which claims priority to U.S. Provisional Patent Application No. 61/121.982 filed on Dec. 10, 2010, the entire contents of which are hereby incorporated by reference for all purposes.

BACKGROUND

A biosensor is a device which measures the presence or level of an analyte in a biological sample. A biosensor may include three main parts: i) Biologically reactive elements sometimes referred to as a reagent. Reagents may include biological materials (e.g., tissues, microorganisms, organelles, cell receptors, enzyme, antibodies, and take acid, etc.), a biologically derived material or biomimic, wherein the reagent may be created by biological engineering; ii) a transducer or detector element which may work in a physiochemical way (e.g., optical, piezoelectric, electrochemical, etc.) to transform the signal resulting from the interaction of the analyte being measured with the reagent into another signal that can be more easily measured and quantified; and iii) associated electronics or signal processors that are primarily responsible for the display of the results m a user-friendly way.

Diabetes mellitus is a worldwide public health problem. This metabolic disorder is caused by a deficiency in, or resistance to, insulin, and can result in hyperglycemia, a condition in which blood glucose concentrations may be higher than the normal range of 80-120 mg/dL (4.4-6.6 mM). Diabetics can take medicine such as insulin to lower their blood glucose concentration but such medicines have the hazard of sometimes lowering the blood glucose to below the normal range and risk unconsciousness, organ damage and in severe cases death. Symptoms and complications may be greatly reduced through patient management and control of blood glucose levels. Consequently, biosensors which measure concentrations of glucose in a patient are in high demand. Indeed, glucose sensing biosensors are incorporated into home blood glucose meters which are widely used by diabetics to accomplish this goal.

Conventional blood glucose meters are generally glucose biosensors that analyze a blood droplet from a patient's finger prick. Biosensors combine a biological sample (in the ease of conventional blood glucose meters, blood droplets) with a physiochemical detector component (i.e., reagent) to allow for the detection of glucose (i.e., analytes) in the blood droplet. An analyte is a substance or chemical constituent that is determined in an analytical procedure. For example, glucose is the analyte in the process used in the blood glucose biosensors. Biosensors can he used for detecting or determining characteristics of any kind of analyte that can be analyzed by biological means. In a glucose biosensor used for home blood glucose monitoring, blood is applied to a test element, such as a disposable test strip, to react with an enzyme (i.e., reagent such as glucose oxidase, GOx) already deposited on the strip. The conventional blood glucose meter may detect a current, which is generally proportional to the glucose concentration in the blood droplet, allowing a calculated reading to be displayed to the patient.

Conventional blood glucose meters often require patients to prick their fingers to obtain a blood droplet. Such procedures may result in pain and discomfort for the patient, as well as an open wound vulnerable to infection, and tissue scarring that ultimately renders a site useless for sampling. In addition, the resulting blood droplet sample may be exposed to external elements which may contaminate the blood droplet sample. Accordingly, sampling and analyzing devices which may generate a biological sample from the patient for glucose testing that does not result in patient harm, preserves the integrity of the biological sample, and produces accurate biosensor results are desired.

SUMMARY OF THE INVENTION

The various embodiment methods and apparatus improve the accuracy of a novel transdermal sampling and analysis device by mitigating the effects of non-analyte chemical species (referred to herein as interferents) upon analyte measurement. Interferents may be defined as biological molecules that cause inaccurate measurements in a biosensing process by falsely presenting the appearance of more or less of the analyte being detected. In the case of glucose detection, for example, an interferent may cause the presence of excess electrons. The excess electrons may result in a higher detected electrical current in the glucose biosensor. Consequently, a higher than actual glucose concentration may be reported to the patient of the transdermal glucose biosensor. The various embodiments and apparatus provide a barrier layer having a charge type which may repel similarly charged interferent molecules in order to prevent the interferents from interacting with a biosensor disposed below the barrier layer. Thus, the interferents may be prevented from causing an inaccurate reading of analyte concentration in a sample.

An embodiment transdermal sampling and analysis device may include a substrate having a first side; at least one disruptor mounted on the first side of the substrate, in which the at least one disruptor is configured to generate a localized heat capable of altering the permeability characteristics of a stratum corneum layer of skin of an organism; a reservoir configured to collect and contain a biological sample; and a biological sensing element comprising at least two sensing electrodes configured to determine the levels of an analyte in the biological sample, in which: a surface of at least one of the sensing electrodes is coated with a sensing layer having a first charge type; and the sensing layer is covered with an anti-interferent barrier layer having at least a second charge type, in which the first charge type is an opposite charge type from the second charge type.

Another embodiment transdermal sampling and analysis device may include a substrate having a first side; at least one disrupter mounted on the first side of the substrate, in which the at least one disrupter is configured to generate a localized heat capable of altering the permeability characteristics of a stratum corneum layer of skin of an organism; a reservoir configured to collect and contain a biological sample; and a biological sensing element that includes at least two sensing electrodes configured to determine the levels of an analyte in the biological sample, in which: a surface of at least one of the sensing electrodes is coated with a sensing layer; and the sensing layer is covered with an anti-interferent barrier layer, in which molecules of the anti-interferent barrier layer are conjugated to molecules of the sensing layer. In such embodiments, the sensing layer may or may not possess a charge.

Another embodiment transdermal sampling and analysis device may include a substrate having a first side; at least one disrupter mounted on the first side of the substrate, in which the at least one disrupter is configured to generate a localized heat capable of altering the permeability characteristics of a stratum corneum layer of skin of an organism; a reservoir configured to collect and contain a biological sample; and a biological sensing element that includes at least two sensing electrodes configured to determine the levels of an analyte in the biological sample, in which: a surface of at least one of the sensing electrodes is coated with a sensing layer, in which the sensing layer has an electron mediator; and the sensing layer is covered with an anti-interferent barrier layer, in which the anti-interferent barrier layer has a charge, and in which the anti-interferent barrier layer repels a charged biological reducing species in the biological sample in order to prevent interaction between the electron mediator and the charged biological reducing species in the biological sample.

An embodiment method of preventing interference from a charged biological reducing species in a transdermal biosensor device may include: creating a solid state sensor in which an enzyme and an electron mediator are immobilized by a polymer to form a sensing layer, in which the polymer is anchored to a sensing electrode; and applying an anti-interferent barrier layer atop the sensing layer, in which charge type repulsion between the anti-interferent barrier layer and the charged biological reducing species prevents interaction between the biological reducing species and the electron mediator.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any embodiment described herein as "exemplary" and/or "example" is not necessarily to be construed as preferred or advantageous over other embodiments.

The term "in situ" is used herein to refer to tests and/or measurements performed using a natural composition/tissue in an environment that is at least partially subject to artificial control. For example, a novel transdermal biosensor may be said to be operating in situ when it is placed on the surface of a patient's skin while it disrupts the stratum corneum continuously to generate a biological fluid sample and analyze the generated biological fluid sample while the biosensor remains in place on the surface of the patient's skin.

The most commonly used and convenient type of biosensor for monitoring small molecule concentrations may be the amperometric biosensor, in which electrons from an enzyme-catalyzed redox reaction may be transferred to an electrode, and the current flow resulting from the transfer of electrons may be used as a measure of the glucose flux, from which the analyte concentration may be deduced. Amperometric biosensors measure the current generated between a working and counter electrode when the potential between them may be maintained at a constant level by means of a potentiostat.

Glucose biosensors designed for patient home monitoring generally measure current produced by the enzymatic oxidation of glucose in an electrochemical cell. The sample used for analysis is often a blood droplet collected from a patient's finger, arm, or other location on the body. In addition to being painful, these biosensors are also designed in a manner to require a relatively large sample to accurately determine analyte concentration. For example, the currently available blood glucose biosensors require at least 300 nl of blood in order to analyze the blood glucose levels. To obtain these larger biological samples, painful and invasive procedures must be employed, which are not desirable.

Another disadvantage of the conventional biosensors is that they require several steps before they can analyze a biological sample. Conventional biosensors require loading a lancing device with a disposable tip, loading a test strip into an analyzer, breaching the skin, collecting the biological samples (e.g., blood), into the test strip, and disposal of the sharp tip and blood-laden test strip. This multi-step process is time consuming and may cause contamination or loss of the biological sample during the collection and/or delivery.

Additionally, if the sharp instruments that are used to breach the epithelium are not disposed of properly, cross-contamination of diseases, such as hepatitis, may result when other persons come in contact with the contaminated sharp instrument. Thus, the development of a non-invasive, single-step glucose biosensor, such as the transdermal glucose biosensor, may be widely used to promote both patient comfort and safety.

A novel, one-step home monitoring glucose biosensor may provide effective in situ measurement of glucose concentration from small quantities of the interstitial fluid collected from the capillary-like channels of the patient's skin. This system (referred to herein as the "transdermal sampling and analysis device" or "transdermal glucose biosensor") is described in U.S. patent application Ser. No. 13/294,368, entitled "Transdermal Sampling and Analysis Device", the contents of which are hereby incorporated by reference for the purpose of describing the systems and methods disclosed therein.

The transdermal glucose biosensor may also enable the entire process of analyzing a biological sample including disrupting the skin cells, collecting biological samples, reacting the biological sample with a biologically reactive element; and sensing the signals generated by the reaction in singular device. In contrast, in in vitro measurements, such as those performed using traditional finger stick glucometers, a biological sample (e.g., ISF) may be collected, and subsequently tested for an analyte (or other measurable property) by submitting it to a remote assay or sensor (e.g., glucose sensor). By incorporating a sampling device and analyzing device in a singular in situ test, a smaller biological sample may be required and the potential for contamination of the biological sample may be dramatically reduced. The time required to obtain a sample and perform an analysis of the sample may be also reduced.

The various embodiment methods and apparatus allow for improved accuracy in real-time analysis of biological samples using a transdermal glucose biosensor. In an embodiment, the biosensor may be a transdermal sampling and analysis device as described in U.S. patent application Ser. No. 13/294,368 entitled "Transdermal Sampling and Analysis Device." The various embodiment methods and apparatus improve the accuracy of a transdermal analysis and sensing device, such as the transdermal glucose biosensor that uses a single-step to obtain and analyze transdermally extracted biological samples.

In such transdermal analysis and sensing device a patient's stratum corneum may be disrupted through the application of localized heat to allow interstitial fluid to permeate from capillary-like channels and may be collected. The collected fluids may be tested for an analyte, such as glucose, by reacting the collected fluids to a biologically reactive element; such as an enzyme (e.g., an oxidoreductase). The products of the biochemical reaction between the collected fluid sample and the biologically reactive element may be analyzed electrochemically to deduce the concentration of the analyte (also referred to as "reactant") from either a potential or an electrical current. The amount of potential or current that is detected may be mapped to determine concentration levels of analytes or characteristics of the collected fluid sample. Once the disruptor unit is removed from the skin, stratum corneum cells become impermeable again by returning to their original formation and closing the capillary-like channels.

Figure 1A:
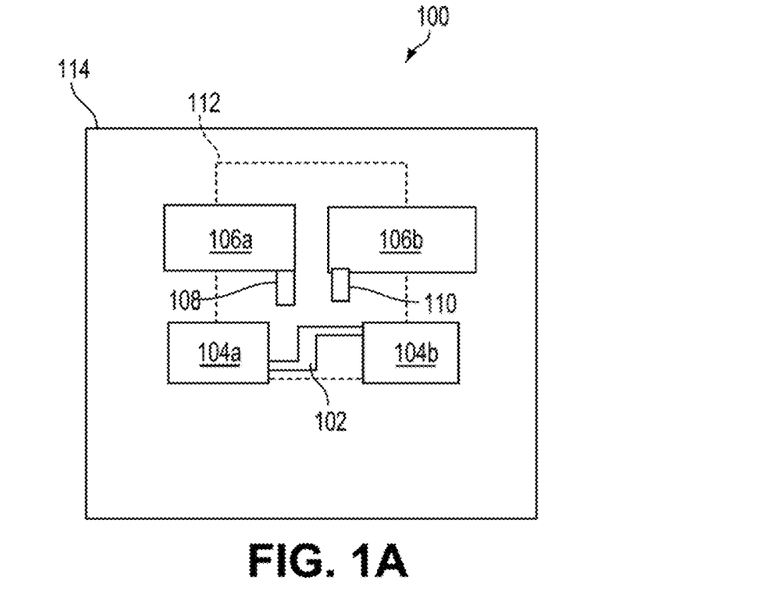
FIG. 1A is a component diagram of a transdermal sampling and analysis device suitable for use with the various embodiments.

FIG. 1A is a block diagram illustrating the functional components of an example transdermal sampling and analysis device 100. A transdermal sampling and analysis device 100 may include a disruptor 102 connected to the positive and negative electrical poles of a signal generator 104a, 104b. In an embodiment, the disruptor 102 may function as a resistive element. The disruptor 102 produces heat as electrical current is applied through the disruptor 102. When placed on the skin, the localized heat generated by the disruptor 102 element may cause disruption to the skin cells facilitating the flow of interstitial fluid onto the surface of the transdermal sampling and analysis device 100. The disruptor 102 may be made from a variety of materials which exhibit the appropriate heating and control properties to provide the precise heating control properties required to disrupt the skin cells without damaging them. After a brief period of increased permeability due to the application of localized heat, the cells return to their normal function.

The materials used to create the disrupter 102 may be selected for relative ease of manufacture as well as cost considerations. Materials such as titanium, tungsten, stainless steel, platinum and gold may be preferably used to form the disruptor 102. In a preferred embodiment, gold may be used to form the disruptor 102.

In an embodiment, when analyzing concentrations of glucose in an obtained biological sample, enzymatic conversion of glucose to gluconolactone may yield electrons which may be captured to generate anodic current between the sensing electrodes 108, 110, also referred to as counter electrode 108 and working electrode 110. The magnitude of the electrical current generated as a result of the chemical reaction may be proportional to the amount or concentration of glucose contained in the obtained biological sample. In an embodiment, a voltage potential may be applied to the counter and working electrodes 108, 110 using a power generator (not shown). Once the obtained biological sample reacts with the reactive biological element coating the electrodes 108, 110, the ions that may be released from the conversion of glucose to gluconolactone facilitate generation of a current across the working and counter electrodes, in such a scenario, the working electrode may function as an anode and the counter electrode may function as a cathode or vice versa. The level of the current may depend on the amount of glucose that is in the biological sample and is converted to gluconolactone. The current that may be generated may be measured by an ammeter, the measurement of which may directly correlate to the level of glucose in the collected biological sample.

A transdermal sampling and analysis device 100 may further include a reservoir 112 for collecting and containing biological samples such as interstitial fluids that flow from capillary-like channels in disrupted stratum corneum. The reservoir 112 may be formed under the disruptor 102 and sensing electrodes 108, 110, When the transdermal sampling and analysis device 100 is place on the subject's skin with the disruptor 102 contacting the skin, the reservoir may effectively be positioned above the disruptor 102 and electrodes 108, 110 to contain the released fluid sample. The reservoir 112 may include a cover or lid to more effectively contain the fluid. A reservoir 112 maybe created using conventional methods known in the art, for example, by the buildup of material by additive process or by subtractive process such as photolithography. A substrate 114 may form the support on which transdermal sampling and analysis device 100 components may be positioned or attached. Because the obtained, biological sample may be analyzed without removing the device from the patient, the process is referred to as an n situ process.

Figure 1B:
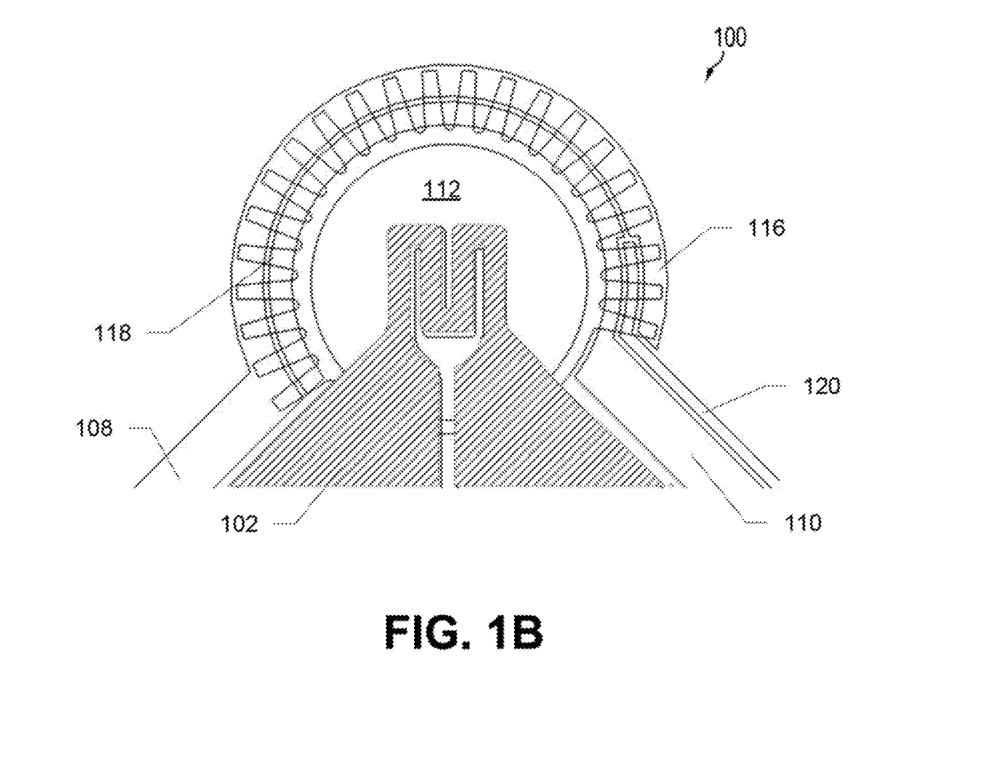
FIG. 1B is a top view of another transdermal sampling and analysis device suitable for use with the various embodiments

FIG. 1B illustrates an alternative embodiment of the transdermal sampling and analysis device 100. The device may include a disruptor 102 having a serpentine configuration, within a collection reservoir 112. Leads capable of coupling the disruptor 102 to a voltage/current source may be extended to the corners of the transdermal sampling and analysis device 100. The disruptor 102 may be also positioned within a hole in a lid layer so that the disruptor 102 may be exposed to and may directly contact the subject's skin for disruption of the stratum corneum and the production of a biological fluid sample. A sensing chamber 116 may form a circular shape around the periphery of the collection reservoir 112. The sensing chamber 116 may contain sensing channels 118 in a radial arrangement. The circular sensing channels 118 may guide the flow of a biological sample through the circular-shaped sensing chamber 116. The sensing chamber 116 may provide the biological fluid sample over counter and working electrodes 108, 110. A reference electrode 120 may optionally be included. A biological fluid sample may be directed over the entire surface of counter and working electrodes 108, 110. The disruptor 102, counter and working electrodes 108, and optional reference electrode 120 may be all formed on a substrate layer.

Many different analysis techniques may be incorporated into the transdermal sampling and analysis unit to determine the levels and concentrations of various analytes in a biological sample. For example, amperometric, coulometric, potentiometric techniques may be each alternative techniques which may be incorporated into the transdermal sampling and analysis device to determine levels or concentrations of analytes in a biological sample. In addition, electrochemical impedance analysis techniques may be incorporated to detect the presence of particular antibodies in a biological sample.

The counter and working electrodes 108, 110 may be made from any of a variety of materials which exhibit satisfactory conductivity characteristics and appropriate to the specific measurement used. In addition, the materials used, to create the electrodes may be selected for relative ease of manufacture as well as cost considerations. Examples of materials exhibiting satisfactory conductivity characteristics for use as the counter and working electrodes 108, 110 may include gold, platinum, silver, carbon or other materials.

Selection of a substrate 114 for the transdermal sampling and analysis device 100 may depend on the coefficient of thermal expansion and conductivity of the material used to make the disruptor 102 of the transdermal sampling and analysis device 100. For example, the substrate 114 may be made of a material which has a coefficient of thermal expansion (CTE) that deviates from the CTE of the material used in the disruptor 102 by less than 50%, and preferably by less than 10%. In a further embodiment, the substrate 114 may be made of a material which has a coefficient of thermal conductivity (CTC) that is lower than 0.5 W/(m·K)

A biologically reactive element, such as an enzyme, may be applied to the first side of the substrate 114. For example, the biologically reactive element may be applied to the working electrode 110, the counter electrode 108 or both. As the stratum corneum is disrupted, interstitial fluid begins to flow through the stratum corneum into the reservoir 112 by capillary action of the structure. The interstitial fluid may be directed to flow into the reservoir 112 and specifically over the surface of the counter and working electrodes 108, 110. The obtained interstitial fluid may come into contact with the biologically reactive element on the surface of the counter and working electrodes 108, 110 causing a chemical reaction that releases energy in the form of electrons. The counter and working electrodes 108, 110 may form anode and cathode of an electrolytic cell, enabling current flow through a device which can measure the current at a controllable potential. Thus, the electrons released from the chemical reaction between the biological sample and biologically reactive element may be converted into electrical signals. The electrical signals generated by the chemical reaction may be measured to determine the amount of a target analyte in the obtained biological sample.

The transdermal sampling and analysis device may be designed to deliver heat to the subject's skin with a power density of 1-10 W per $mm^2$. In a preferred embodiment the disruptor delivers heat to the subject's skin with a power density of 2-5 W per $mm^2$. The transdermal sampling and analysis devices may be made using a variety of different disruptor configurations. The size and shape of the disruptor may affect its resistive characteristics and consequently, its ability to generate a localized heat, in addition, the material selected to form the disruptor may also affect its resistive characteristics and consequently, its ability to generate a localized heat. As with electrode material selection, disruptor materials may be selected from a wide variety of materials exhibiting satisfactory electrical conductance/resistive properties such that sufficient heat may be generated when specific voltages are applied to the disruptor leads. In addition, thermal conduction and resistance characteristics should be observed in an optimal disruptor material. Finally, ease of manufacturing processing and cost may determine the final selection of disruptor material. For example, a disruptor may be made of nichrome, titanium, tungsten, or gold. In a preferred embodiment, the disruptor may be made from gold.

Since different subjects may have different skin thickness levels, calibration of the transdermal sampling and analysis device may be required to generate sufficient heat for obtaining the most amounts of biological samples with the least amount of sensation. Thus, the level and duration of the temperature of the disruptor may be adjusted for different subjects. Preferably, disruption of the skin may occur when heat of 140° C. from the disruptor may be supplied to the skin surface for duration of about 140 ms. However, the in situ measurement employed in the transdermal glucose biosensor—that is, the performing the glucose sensing concurrently with, and in the same device as, skin disruption and collection of ISF—has been shown to negatively impact the accuracy of the results. Specifically, in vitro tests using the same components and biological samples yielded accurate measurements of glucose concentration that were not replicated in situ. It is believed that the inaccurate results from the transdermal glucose biosensor may be caused by interference from other biological species in the ISF, a problem, that is therefore not encountered in traditional glucose sensing devices (e.g., finger stick glucometers). The various embodiments provide methods and structures for preventing, and/or reducing the level of, interference in the transdermal glucose biosensor and/or other in situ biological sensing methods or devices.

In general, the concept behind a glucose biosensor is the fact that an immobilized enzyme such as glucose oxidase (GOx) catalyzes the oxidation of glucose by molecular oxygen producing gluconic acid and hydrogen peroxide. In order to work as a catalyst, the enzyme (e.g., GOx) requires a redox cofactor (e.g., flavin adenine dinucleotide (FAD) in GOx). FAD works as the initial electron acceptor and is reduced to $FADH_2$. In a typical reaction cycle, a substrate $X-H_2$ (e.g., glucose) binds to the enzyme active site and interacts with the flavin, $FAD^+$ to generate the oxidized product X (e.g., glucolactone) and the reduced flavin, FADH$_2$. This is shown in Eq. 1 below:

$$X\text{-}H_2 + GOx\text{-}FAD \rightarrow GOx\text{-}FADH_2 + X \quad (Eq. 1)$$

The oxidized product dissociates, and the cofactor is regenerated by reacting with oxygen, leading to the formation of hydrogen peroxide. The oxygen binds to the active site of the enzyme and reacts with the reduced flavin, regenerating FAD and being reduced to H$_2$O$_2$, shown in Eq. 2 below:

$$GOx\text{-}FADH_2 + O_2 \rightarrow GOx\text{-}FAD + H_2O_2 \quad (Eq. 2)$$

Some glucose biosensors (e.g., Continuous Glucose Monitors (CGMs)) measure the amount of amount of hydrogen peroxide produced in the reaction that used oxygen as reducer of the electrode. However, amperometric measurement of hydrogen peroxide requires a high operation potential for high selectivity. Further, oxygen has restricted solubility in biological fluids. Therefore, improved biosensors may use redox mediators that replace oxygen in carrying electrons from the enzyme to the surface of the working electrode. For example, test strips used in home glucose monitors may contain the enzyme and a mediator. The mediator may be reduced by the enzyme, and the reduced form of the mediator is reoxidized at an electrode. The oxidation of the mediator by the electrode provides an amperometric signal.

Figure 2:
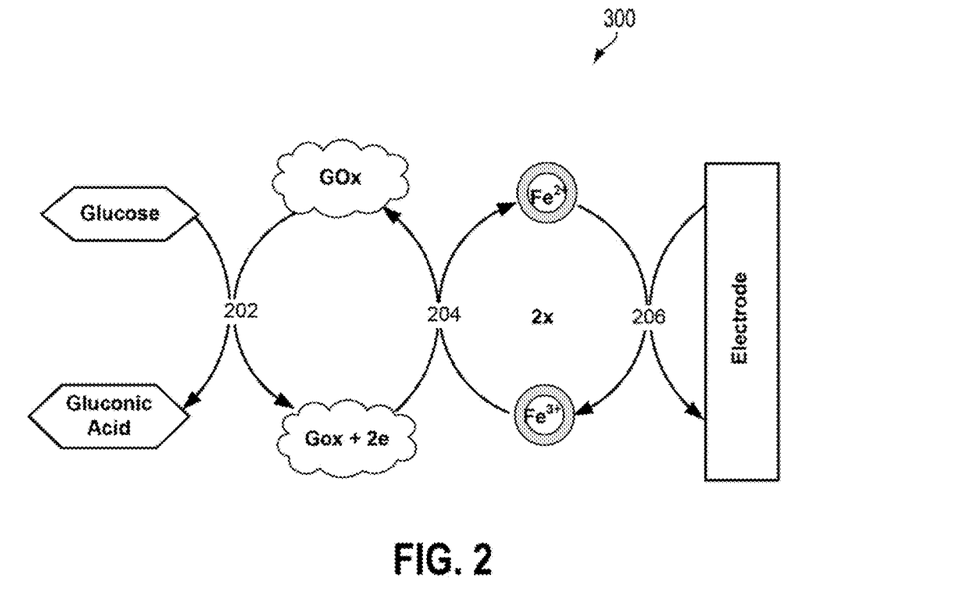
FIG 2 is a schematic illustration of an example reaction in glucose biosensors.

An example reaction shown in FIG. 2 illustrates the general steps that may occur to generate glucose concentration measurements in a basic home blood glucose monitor that uses GOx. GOx may catalyze a breakdown of glucose in the interstitial fluid to gluconolactone, step 202. GOx may be reoxidized with an excess of a mediator reagent, such as a ferricyanide (Fe(CN)$_6^{3-}$), ferrocene (i.e., "Fc") (Fe(C$_5$H$_5$)$_2$), or osmium bipyridyl complex (C$_{20}$H$_{16}$C$_{12}$N$_4$Os). For example, in step 204 GOx may be reoxidized by reducing the oxidized form of a mediator (i.e., ferrocenium), converting it to its reduced form (i.e., ferrocene). The mediator in torn may be reoxidized at the electrode to generate an electrical current.

The electron mediator may transfer electrons to the working electrode, where anodic potential has been applied such that the mediator may be oxidized. The oxidized mediator may be then able to accept another electron from the glucose conversion reaction to repeat the process. For example in step 206, ferrocene may be reoxidized by reducing the electrode, step 206. The total charge passing through the electrode is proportional to the amount of glucose in the blood that has reacted with the enzyme. Since each ferrocene undergoes one-electron oxidation, the oxidation and reduction steps 204 and 206 between ferrocene and ferrocenium may be performed on two ferrocenes for every glucose molecule in order to transfer to the electrode both electrons that were transferred by GOx. The above reactions are provided merely as examples, and may differ significantly from small variations in the enzyme, electrode structure, or mediator. The number of cycles/molecules used to transfer electrons for each particular mediator is specific to the redox reaction that that mediator undergoes, which may or may not be similar to the ferrocene/ferroocenium reactions.

In various embodiments, the transdermal glucose biosensor may have a solid state mediated sensor. Such sensor may include a film disposed on the surface of a sensing electrode. The film may be formed by a polymer, a mediator conjugated (i.e., covalently bonded) to the polymer, and an enzyme immobilized, by the polymer with conjugated mediator.

In one embodiment, an electron mediator may be ferrocene (Fc) may be conjugated to the backbone of linear poly(ethyleneimine) to create LPEI-Fc. GOx and l-PEI-Fc may be mixed in various ratios and dispensed over the sensing electrodes in the analysis chamber along with known quantities of crosslinker such as ethylene glycol diglycidyl ether (EGDGE) resulting in a crosslinked LPEI-Fc/GOx matrix that is smooth and uniform at the air/electrolyte interface. Example mediators that may be used include, but are not limited to, ferrocene, osmium bipyridine complexes, ruthenium phthalocyanine complexes, ferrocenecarboxaldehyde (C$_{11}$H$_{10}$FeO), a quinone, a tetrathialfulvalene (TTF), a tetracyanoquinodimethane (TCNQ), a thionine, etc.

Figure 3:
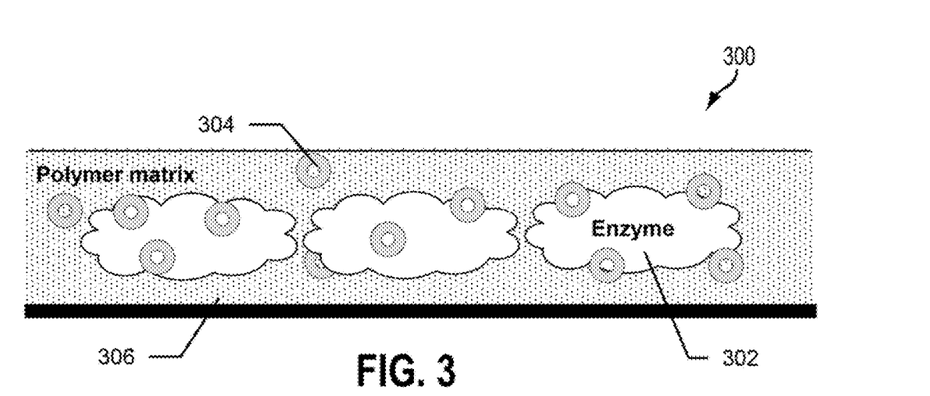
FIG. 3 is a schematic illustration of a solid state sensing agent without a hairier layer in a transdermal glucose biosensor.

FIG. 3 illustrates the composition of an example solid state mediator sensor 300. An enzyme 302 (for example, GOx, glucose dehydrogenase (GDH), etc.) may be immobilized by the polymer layer 306 (e.g., LPEI), and a redox mediator 304 (e.g., ferrocene, ferricyanide, etc.) may be conjugated or tethered (i.e., connected to a long carbon chain that is conjugated) to the polymer layer 306 (e.g., LPEI) which conducts electrons from FADH$_2$ to an electrode.

Figure 4A:
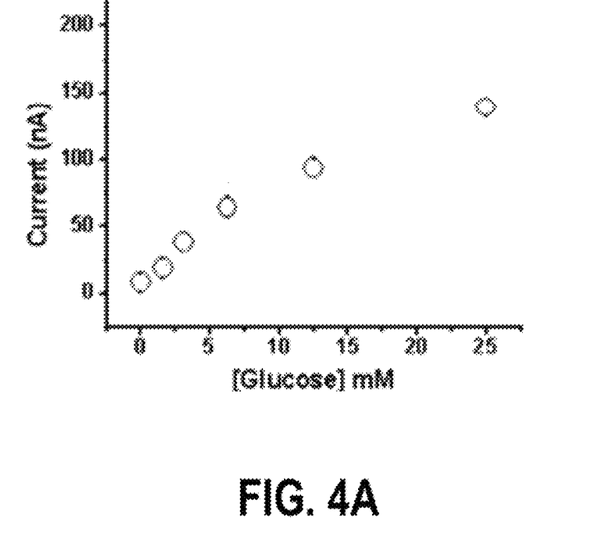
FIGS. 4A and 4B are graphs showing chronoamperometric current measurement results for glucose concentrations in sample solid state sensing agents without barrier layers.

FIG. 4A shows results from in vitro testing of a solid state mediator sensor replicating conditions of a novel transdermal glucose biosensor. As expected, the plotted data show current generated at 30 seconds as a function of glucose concentration, and show high linearity in sensing range of the sensor to a concentration of 12 mM. For example, sensitivity of the particular sensor reached values as high as 50 µA-mM-1·cm$^2$. Thus, when operated in vitro away front the patient's body the novel transdermal glucose biosensor accurately measures glucose concentrations.

Figure 4B:
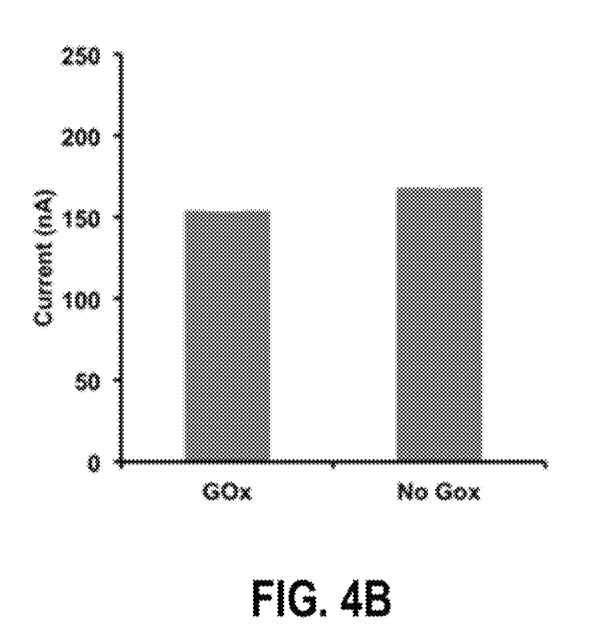

However, when operated in situ, it maybe observed that a solid state mediator-type sensor in a transdermal glucose biosensor may return inaccurate readings of glucose concentration levels. FIG. 4B shows results from in situ testing of a solid state mediator-type sensor in a transdermal glucose biosensor, both with and without GOx, in a transdermal glucose biosensor. In particular, at the normal human glucose level (5.5 mM), the current generated is shown in the in vitro measurements in FIG. 4A at around 75 nA, which is the expected in situ measurement. However, the in situ data show a current of around 150 nA. Further, when no GOx is present, it is expected that no content is generated; yet the in situ data for the control sensor (i.e., electrode without GOx) is shown to have similar performance characteristics as that of the actual sensor (with GOx), showing that the presence or absence of GOx did not make any difference in the measured current. While not conclusive, it may be postulated that unknown interferents may be produced by a patient's body that result in excess electrons in a generated biological fluid sample. The presence of such interferents may result in the inaccurate readings of glucose concentration levels. Such results indicate false positive glucose measurements, negating the usefulness of the sensor. It is believed that during the in situ analysis utilized with the novel transdermal sampling and analysis device, interferents produced by the subject's body are responsible for currents of roughly double in magnitude the expected values as predicted by the data from titered glucose solutions in vitro.

The presence of redox species in the interstitial fluid may be suggested by these results. Without wishing to be bound to a particular theory, it is believed that due to the integration of collection and analysis in the same unit, various biological species in the ISF interfere with the glucose measurements in a manner that does not occur when the collection and sensing steps are performed in separate steps (i.e., conventional in vitro finger stick sensors). That is, the mediator which, in correct processing, is reduced by the oxidation of glucose, may instead be reduced by redox species in ISF that may be strong reducing agents. This transfer of electrons by other molecules may result in falsely elevated glucose concentration readings, and the amount of charge measured from the electrodes would no longer be in proportion with the levels of glucose.

Figure 5A:
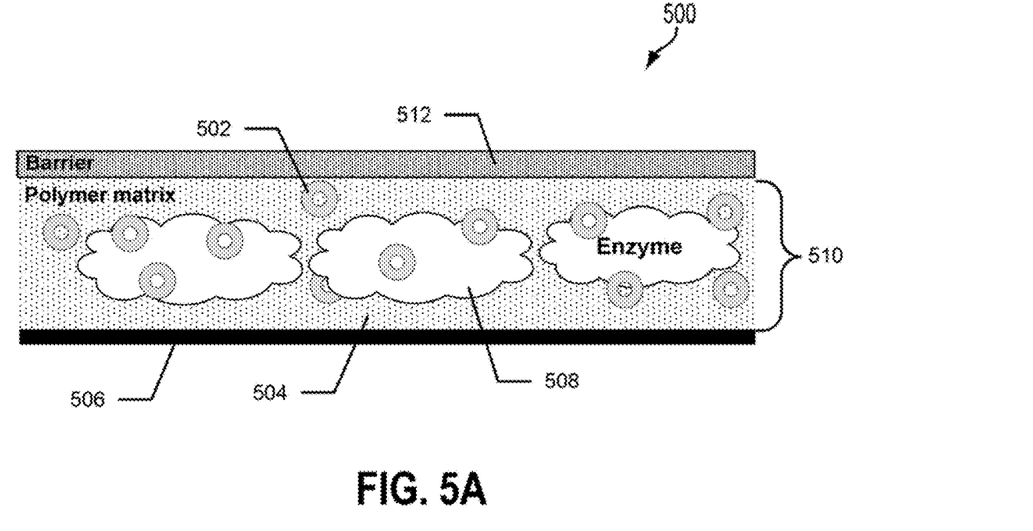
FIGS. 5A and 5B are schematic illustrations of an embodiment solid state sensing agent with a barrier layer in a transdermal glucose biosensor.

Thus, the various embodiments disclosed herein provide a barrier layer for a transdermal glucose biosensor in order to prevent or reduce interference from redox species in the ISF. FIG. 5A illustrates an example transdermal glucose biosensor fabricated with an anti-interferent barrier layer 512. In an embodiment, a mediator 502 (e.g., ferrocene, osmium bipyridine complex, etc.) may be conjugated to a polymer 504 which is anchored to a sensing electrode 506. The polymer may be, for example. Linear poly(ethyleneimine) (LPEI). A glucose catalyzing enzyme 508 (e.g., GOx, GDH, etc) may be mixed with, dispensed with, and immobilized by the polymer 504. In this manner, a sensing layer 510 (i.e., sensing reagent) may be formed by a matrix of an enzyme and a mediator linked with a polymer (e.g., GOx-LPEI-Fc), wherein the mediator is linked with the polymer and the enzyme is "captured."

In an embodiment, a charged barrier layer 512 may be applied atop the sensing layer 510 to prevent interfering species from reaching the mediator 502. By forming a charged barrier layer 512 atop the sensing layer 510, charge type repulsion between the anti-interferent barrier layer and the charged biological reducing species prevents interaction between the biological reducing species and the electron mediator. The barrier layer 512 may be formed using a variety of materials, including but not limited to, one or more polyionic polymers. The charged barrier layer 512 may be associated to the sensing layer 510 using a variety of forces. For example, a charge interaction between the sensing layer 510 and the charged barrier layer 512 may attract the barrier layer 512 to the sensing layer 510. Alternatively, the charged barrier layer 512 may be conjugated (covalently bonded) to a sensing layer 510. In such embodiments the sensing layer 510 may be uncharged. In still other embodiments, the barrier layer 512 may be held to the sensing layer 510 through the van der Waals forces which attract the molecules of the barrier layer 512 to the molecules of the sensing layer 510. In an embodiment, the barrier layer 512 may be formed as a monolayer of alginates or other anionic naturally occurring polymers.

Figure 5B:
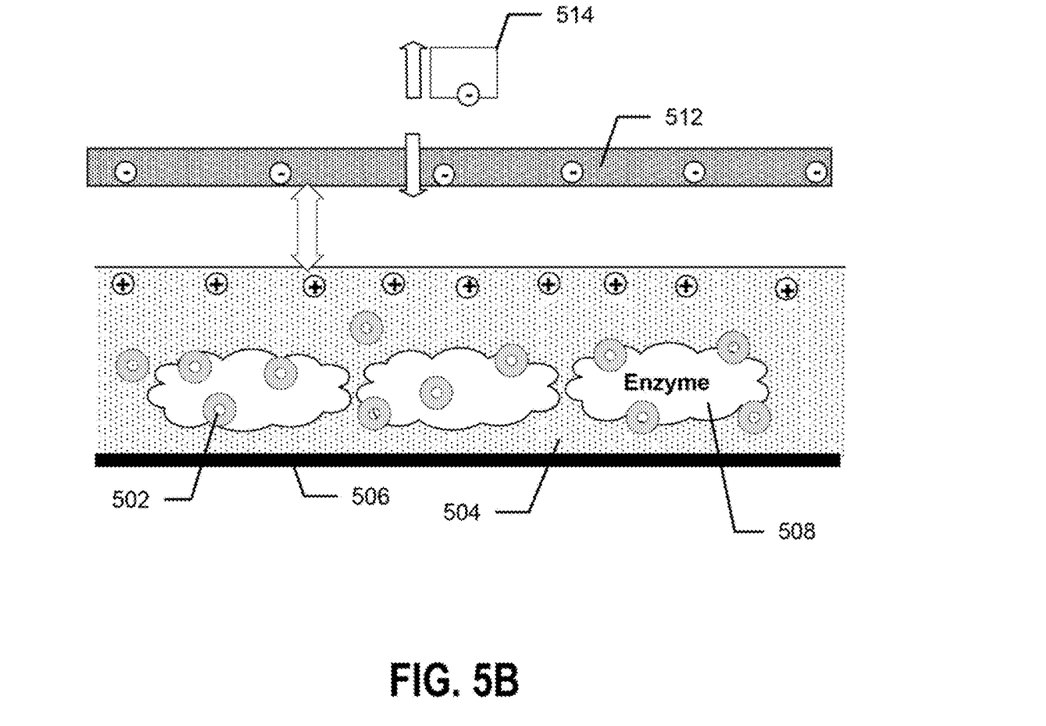

FIG. 5B illustrates the interaction of an embodiment sensing layer 510, barrier layer 512, and potential interferents 514 when an anionic polymer is used to make the barrier layer 512 and LPEI is used in the sensing layer matrix. LPEI is a polycationic polymer, which every third atom along the polymer chain as a protonable amine group. Thus, a negatively charged barrier species (e.g., alginate) may interact with a positively charged sensing layer 510 to provide a barrier layer 512 in the various embodiments. As previously discussed, it is believed that interferent molecules may be reducing agents in the ISF that come into contact with the mediator. As such, an interferent molecule, such as interferent 514, may be negatively charged and may therefore be repelled by an anionic barrier layer such as barrier layer 512. In an alternative embodiment, a polyanionic polymer may be used instead of a polycationic polymer to form the sensing layer 510, and a polycationic compound may be used to form a barrier layer 512.

In an alternative embodiment (not shown), a barrier layer may be formed by conjugating a barrier layer material to the sensing layer. For example, a barrier layer material may be conjugated to the molecules on the surface of the sensing layer (e.g., GOx/LPEI/Fc matrix). In an embodiment, molecules of the barrier layer material may be conjugated to amine groups of the polymer in the sensing layer (e.g., LPEI). By conjugating the barrier layer material to the amino groups on the surface of the l-PEI-Fc film it may become possible to tailor the surface properties. The barrier layer may be charged, thereby repelling charged interferent molecules in the same manner as described above with respect to FIG. 5B. In another alternative embodiment (not shown), a barrier layer may be formed due to van der Waals forces (i.e., weak, induced dipole forces) between molecules or the barrier layer 512 material and the sensing layer 510. The barrier layer 512 material may be applied to the sensing layer 510 using processes that include, but are not limited to, chemical and physical deposition processes.

Thus, in an embodiment device 100 that uses interstitial fluid to test for glucose, the biologically reactive element glucose oxidase (GOx) may be applied to the sensing electrodes 108, 110 in a matrix with the electron mediator ferrocene (Fc) and a polymer linear poly(ethyleneimine) (LPEI) to form the sensing reagent (LPEI-Fc/GOx matrix).

Figure 6A:
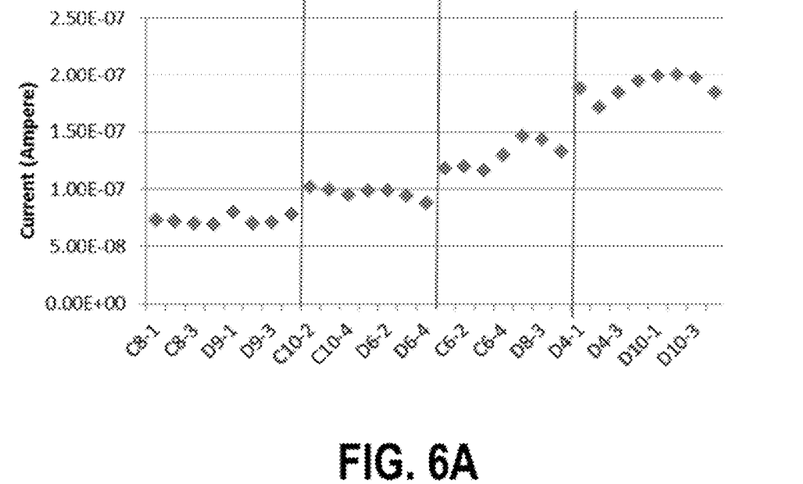
FIGS. 6A and 6B are graphs showing chronoamperometric current measurement results for glucose concentrations in embodiment solid state sensing agents in a transdermal glucose biosensor.
Figure 6B:
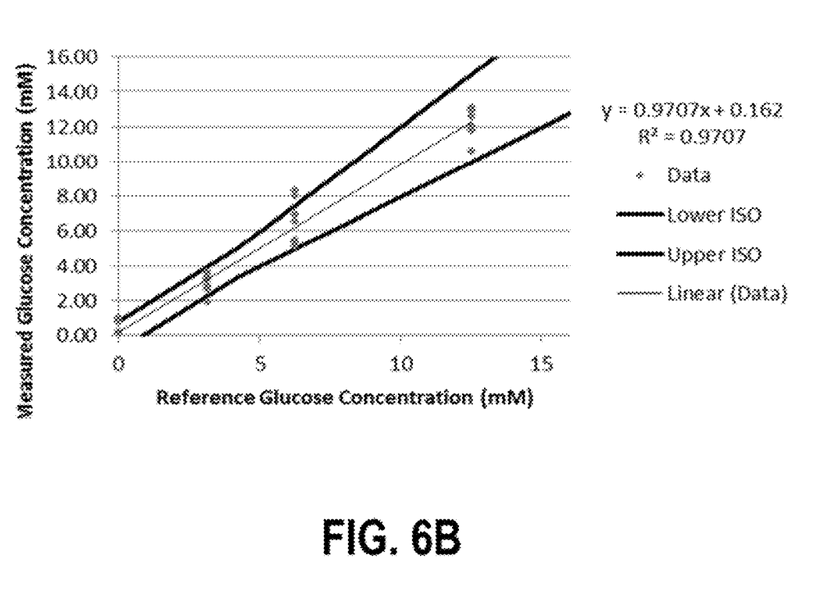

FIG. 6A shows results from in vitro testing of a solid state sensor with anti-interferent barrier layer. The plotted data show current generated by the sensor as a function of known glucose concentrations (0.0, 3.125, 6.25 and 12.5 mM titered solutions in phosphate buffered saline). The data show that the sensors responded accurately in a linear fashion with respect to glucose concentration. FIG. 6B is a regression analysis of the results in FIG. 6A showing that the embodiment sensors behave within the International Organization for Standardization (ISO) limits for in vitro glucose test systems. Consequently, the embodiment solid state sensor with anti-interferent barrier layer may be deemed to be an accurate glucose sensor.

Figure 7:
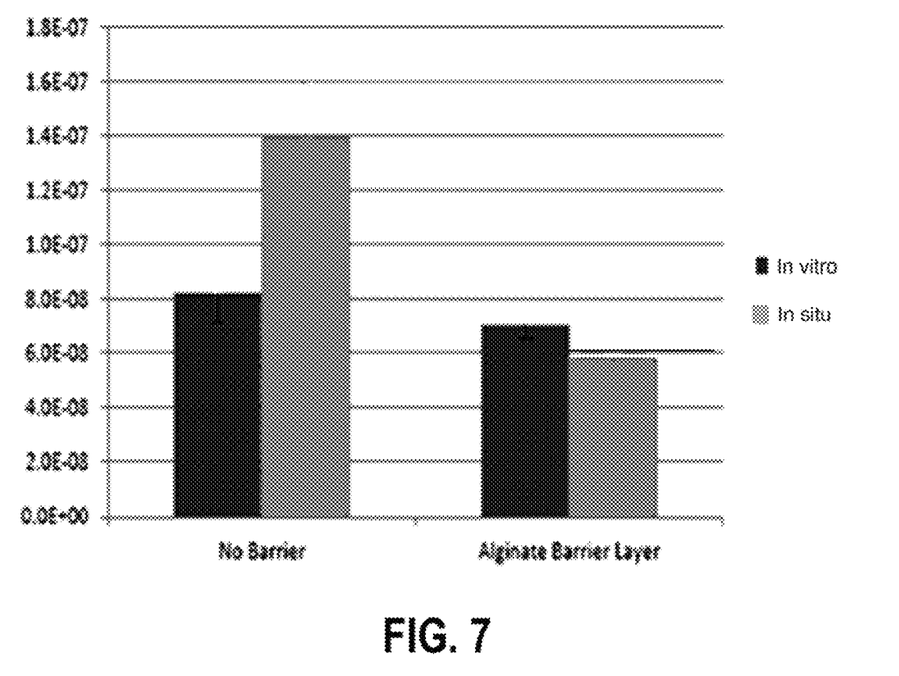
FIG. 7 is a graph comparing chronoamperometric current measurement results for glucose in solid state sensing agents with and without barrier layers.

The improved accuracy in glucose concentration analysis provided by the anti-interferent barrier layer may be illustrated in FIG. 7. FIG. 7 compares results testing of a solid state sensor without an anti-interferent barrier layer and with an alginate barrier layer. The plotted data compare in situ and in vitro sensor measurements on 90 mg/dl ISF. Thus, it is shown that the alginate barrier layer allows in situ measurements to approximate the in vitro measurements, as opposed to the increased response seen without the barrier.

In an embodiment, a GOx-LPEI-Fc sensing layer may be fabricated by combining, in a ratio by volume of 7:1:0.1, the following solutions: 20 mg/ml solution in a 2-(N-Morpholino)EthaneSulfonic acid (MES) buffer of LPEI (e.g., MW ~25 kDa) with conjugated Fc; 20 mg/ml solution in a MES buffer of GOx; 1% (w/w) EthyleneGlycol DiGlycidylEther (EGDGE) solution in water.

In an embodiment, the sensing layer may be deposited using a Sienion S3 piezo-type liquid dispensing system (Scienion Ag, Berlin, Germany). A volume of 5 $\mu l/cm^2$ may be applied and allowed to dry overnight. In another embodiment, the sensing layer may be applied by dropper, spray, dip, or other coating method appropriate to the sensor system. Thickness of the sensing layer may be, for example, between 0.1 and 10 $\mu m$, preferably between 0.2 and 5 $\mu m$, and most preferably between 0.5 and 2 $\mu m$.

In an embodiment, an alginate barrier layer may be created by soaking the sensing element (GOx/LPEI/Fc matrix and sensing electrode) in a 0.5% (w/v) sodium alginate ($NaC_6H_7O_6$) solution (i.e., sodium salt of alginic acid) in deionized water for thirty minutes. The sensing element may be removed from the solution and rinsed with deionized water, and dried for 18 hours. In this manner, a barrier layer may be formed as a self-assembled alginate monolayer. Parameters for creating a barrier layer according to the various embodiments, including concentration, temperature, and time, may be adjusted to achieve optimal results.

In one embodiment, a sodium alginate may be selected based on a low molecular weight. For example, a commercially produced sodium alginate may be selected from a range of molecular weights that are below 200 kDa, and preferably that are below 75 kDa.

Figure 8:
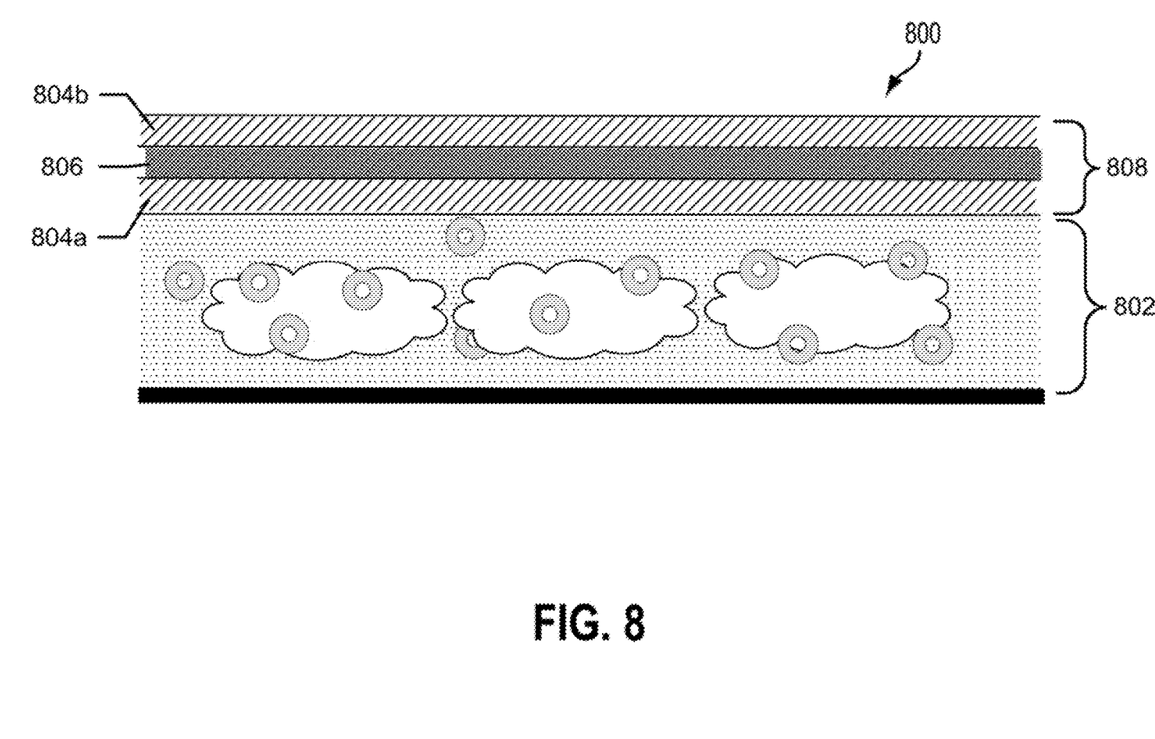
FIG. 8 is a schematic illustration of an embodiment solid state sensing agent without multiple barrier layers in a transdermal glucose biosensor.

In another embodiment, a multi-layer barrier layer may be formed by applying an initial barrier layer 8 onto the sensing layer, and applying a plurality of barrier layers with alternating charges (e.g., anionic, cationic, anionic, etc.) atop the first barrier layer. The plurality of layers, which create a "composite" barrier layer, may improve the selectivity of the barrier. In an embodiment, the initial barrier layer may be an anionic polymer (e.g., alginate), atop which alternating layers of a cationic polymer (e.g., chitosan) and alginate may be formed.

FIG. 8 illustrates an example sensing element 800 that may be formed from barrier layer materials with alternating charges atop a sensing layer 802. For example, initial barrier layer 804a and barrier layer 804b may be a barrier material with a first charge (e.g., anionic), and barrier layer 806 may be a barrier material with an opposite charge (e.g., cationic). The plurality of layers may provide a composite barrier layer 808 with improved selectivity. Although composite barrier layer 808 is formed from three barrier layers with alternating charges, it is provided only as an example. One of ordinary skill in the art would understand that the plurality of barrier layers that form composite barrier layer 808 may be more than three.

In another embodiment, a charged barrier layer (e.g., a cationic or anionic polymer) may be conjugated to the polymer in the sensing layer, on top of which additional layers of alternating charges (e.g., anionic layer, cationic layer, etc.) may be formed (e.g., by charge interaction) to make a composite barrier layer.

Other compounds that may be used in the various embodiments to immobile the mediator and sensor in the sensing layer, or used to form the barrier layer, include, but are not limited to, the following polyions: poly(styrene)-co-styrene sodium sulfonate (NaPSS); polyvinylsilane (PVS); poly {1-4[4-(3-carboxy-4-hydroxyphenylazo) benzenesulfonamido]-1,2-ethanediyl sodium salt}; (PAZO); poly (1-acrylamido-1-methyl-1-propane sulfonic acid) (PAPSA); Poly [bis(4-phenyl)(2,4,6-trimethylphenyl) amine](PTAA); poly (2-acrylamido-2-methyl-1-propanesulfonic acid) (PAMPSA); polystylenemethylenediethylmethylamine (PSMDEMA); poly(allylamine hydrochloride) (PAH); precursors to poly(p-phenylenevinylene) (Pre-PPVs); poly (diallyldimethylammonium chloride) (PDDA); polyetherimide (PEI); poly(p-pyridyl vinylene) (PHPyV); and sulfonated polyaniline (SPAn).

The transdermal sampling and analysis devices of the various embodiments may be manufactured using different methods and materials. Manufacturing methods for an embodiment transdermal sampling and analysis device maybe disclosed in the related International Application Number PCT/US2006/023194, filed Jun. 14, 2006, entitled "Flexible Apparatus and Method for Monitoring and Delivery," which claims priority to the International Application Number PCT/US2005/044287, entitled "Apparatus and Method for Continuous Real-Time Trace Bimolecular Sampling, Analysis and Deliver," filed on Dec. 9, 2005, which are attached hereto as Appendices A and B. The manufacturing of an embodiment transdermal sampling and analysis device 200 is also disclosed in the publication entitled "Novel Non-Intrusive Trans-Dermal Remote Wireless Micro-Fluidic Monitoring System Applied to Continuous Glucose and Lactate Assays for Casualty and Combat Readiness Assessment" by John F. Currie, Michael M. Bodo and Frederick J. Pearce, RTO-MP-HFM-109:24-1, Aug. 16, 2004. A copy of the publication is attached hereto as Appendix C. The entire contents of all of the related applications and publication are incorporated by reference herein.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

While the invention has been described in detail with respect to specific embodiments thereof, it will be apparent to those skilled in the art that various alterations, modifications and other changes may be made without departing from the scope of the embodiments described herein. It is therefore intended that all such modifications, alterations and other changes be encompassed by the claims. Further, any reference to claim elements in the singular, for example, using the articles "a/" "an" or "the" is not to be construed as limiting the element to the singular.

What is claimed is:

1. A transdermal sampling and analysis device comprising:
    a substrate having a first side;
    at least one disruptor mounted on the first side of the substrate, wherein the at least one disruptor is configured to generate a localized heat capable of altering permeability characteristics of a stratum corneum layer of skin of an organism;
    a reservoir configured to collect and contain a biological sample; and
    a biological sensing element comprising:
        a sensing chamber forming a circular shape around a periphery of the reservoir;
        at least two sensing electrodes configured to determine levels of an analyte in the biological sample; and
        circular sensing channels configured to guide the biological sample through the sensing chamber, wherein the biological sample is directed over an entire surface of each of the at least two sensing electrodes;
    wherein:
        a surface of at least one of the sensing electrodes is coated with a sensing layer having a first charge type; and
        the sensing layer is covered with an anti-interferent barrier layer having at least a second charge type, wherein the first charge type is an opposite charge type from the second charge type.

2. The transdermal sampling and analysis device of claim 1, wherein the sensing layer comprises an enzyme, an electron mediator, and a polymer.

3. The transdermal sampling and analysis device of claim 2, wherein the biological sample is interstitial fluid (ISF), and wherein the enzyme is an oxidoreductase.

4. The transdermal sampling and analysis device of claim 3, wherein the oxidoreductase is glucose oxidase (GOx).

5. The transdermal sampling and analysis device of claim 2, wherein:
the polymer comprises a polycationic polymer; and
the anti-interferent barrier layer comprises a polyanionic polymer.

6. The transdermal sampling and analysis device of claim 5, wherein the polycationic polymer comprises a linear poly(ethylenimine) (LPEI).

7. The transdermal sampling and analysis device of claim 5, wherein the polyanionic polymer comprises an alginate.

8. The transdermal sampling and analysis device of claim 1, wherein the anti-interferent barrier layer comprises:
a composite barrier layer comprising:
a first anti-interferent barrier layer having the second charge type; and
a second anti-interferent barrier layer having the first charge type, wherein the second anti-interferent barrier layer is disposed on top of the first anti-interferent barrier layer.

9. The transdermal sampling and analysis device of claim 8, wherein the composite barrier layer comprises a plurality of alternating first anti-interferent barrier layers and second anti-interferent barrier layers.

10. The transdermal sampling and analysis device of claim 2, wherein the electron mediator is selected from the group consisting of a ferrocene, osmium bipyridine complexes, ruthenium phthalocyanine complexes, a quinone, a tetrathialfulvalene (TTF), a tetracyanoquinodimethane (TCNQ), and a thionine.

11. The transdermal sampling and analysis device of claim 8, wherein the first anti-interferent barrier layer comprises alginate.

12. The transdermal sampling and analysis device of claim 8, wherein the first anti-interferent barrier layer comprises an alginate monolayer; and
the second anti-interferent barrier layer comprises chitosan.

13. The transdermal sampling and analysis device of claim 11, wherein the alginate comprises a salt of alginic acid that is less than 200 kDa.

14. The transdermal sampling and analysis device of claim 13, wherein the alginate comprises a salt of alginic acid that is less than 75 kDa.

15. A method of preventing interference from a charged biological reducing species in a transdermal biosensor device, comprising:
creating a reservoir configured to collect and contain a biological sample containing the biological reducing species;
creating a sensing chamber forming a circular shape around a periphery of the reservoir;
creating a solid state sensor wherein an enzyme and an electron mediator are immobilized by a polymer to form a sensing layer, wherein the polymer is anchored to a sensing electrode;
applying an anti-interferent barrier layer atop the sensing layer, wherein charge type repulsion between the anti-interferent barrier layer and the charged biological reducing species prevents interaction between the charged biological reducing species and the electron mediator; and
creating circular channels configured to guide the biological sample through the sensing chamber, wherein the biological sample is directed over an entire surface of the solid state sensor.

16. The method of claim 15, wherein the anti-interferent barrier layer is associated with the sensing layer via charge interaction.

17. The method of claim 15, wherein applying the anti-interferent barrier layer atop the sensing layer comprises applying a composite barrier layer atop the sensing layer, wherein the composite barrier layer comprises:
a first anti-interferent barrier layer having a first charge type, wherein the first anti-interferent barrier layer is associated with the sensing layer via charge interaction; and
a second anti-interferent barrier layer having a second charge type, wherein the second anti-interferent barrier layer is disposed on top of the first anti-interferent barrier layer.

18. The method of claim 17, wherein applying the composite barrier layer atop the sensing layer comprises:
applying an initial first anti-interferent barrier layer atop the sensing layer; and
applying a plurality of alternating second anti-interferent barrier layers and first anti-interferent barrier layers atop the initial first anti-interferent barrier layer.

19. The method of claim 15, wherein the anti-interferent barrier layer is conjugated to the sensing layer.

* * * * *